United States Patent
Kalota

(10) Patent No.: US 7,456,318 B2
(45) Date of Patent: Nov. 25, 2008

(54) PROCESS FOR PREPARING BENZYLATED AMINES

(75) Inventor: Dennis J. Kalota, Fenton, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 44 days.

(21) Appl. No.: 11/722,767

(22) PCT Filed: Nov. 2, 2005

(86) PCT No.: PCT/US2005/039469

§ 371 (c)(1), (2), (4) Date: Jun. 25, 2007

(87) PCT Pub. No.: WO2006/073547

PCT Pub. Date: Jul. 13, 2006

(65) Prior Publication Data

US 2008/0188685 A1 Aug. 7, 2008

Related U.S. Application Data

(60) Provisional application No. 60/641,843, filed on Jan. 6, 2005.

(51) Int. Cl.
 *C07C 209/08* (2006.01)
 *C07C 211/17* (2006.01)
 *C07C 211/27* (2006.01)
(52) U.S. Cl. .................. 564/376; 564/445; 564/454
(58) Field of Classification Search .................. None
 See application file for complete search history.

(56) References Cited

U.S. PATENT DOCUMENTS

| 1,854,553 | A | 4/1932 | Livingston |
| 2,490,813 | A | 12/1949 | Hughes et al. |
| 2,789,138 | A | 4/1957 | Heinzelman et al. |
| 2,987,548 | A | 6/1961 | Magee |
| 4,338,255 | A | 7/1982 | Terashima et al. |
| 4,418,218 | A | 11/1983 | Terashima et al. |
| 5,198,587 | A | 3/1993 | Imai et al. |
| 5,220,068 | A | 6/1993 | Knoll et al. |
| 5,449,828 | A | 9/1995 | Nad et al. |
| 5,536,877 | A | 7/1996 | Hammer et al. |
| 6,399,828 | B1 | 6/2002 | Boswell et al. |
| 6,759,554 | B2 | 7/2004 | Buchwald et al. |
| 2003/0017464 | A1 | 1/2003 | Pohi |
| 2003/0065187 | A1 | 4/2003 | Buchwald et al. |
| 2004/0019216 | A1 | 1/2004 | Buchwald et al. |

FOREIGN PATENT DOCUMENTS

| EP | 0713858 | 5/1996 |
| FR | 2068394 | 8/1972 |

OTHER PUBLICATIONS

Vree et al., Some physico-chemical properties of amphetamine and related drugs, Journal of Pharmacy and Pharmacology, 1969, 21, 774-5.

*Primary Examiner*—Brian J Davis

(57) ABSTRACT

This present invention relates to a process for preparing benzylated amines by the reaction of an amine selected from methamphetamine and propylhexedrine with benzyl halide. Numerous improvements are obtained by employing the amine in molar excess with respect to benzyl halide, preferably in a molar ratio of 2 to 1. The excess amine is employed to selectively neutralize by-product acid as the amine salt. The amine salt is then separated from the reaction mixture and basified to reclaim starting amine for recycle to the process.

32 Claims, No Drawings

PROCESS FOR PREPARING BENZYLATED AMINES

CROSS REFERENCE TO RELATED APPLICATIONS

This application is a national stage application of PCT/US2005/039469, filed Nov. 2, 2005, which claims the benefit of U.S. Provisional Application No. 60/641,843 filed Jan. 6, 2005.

BACKGROUND OF INVENTION

This invention relates to an improvement in the production of benzylated amines by the reaction of an amine with a benzyl halide. In particular this invention provides a high-yield process wherein a key by-product of the reaction, hydrogen halide, is removed from the system in an efficient manner.

The production of benzphetamine by the reaction of methamphetamine with benzyl chloride produces large amounts of hydrogen chloride (HCl) by-product that must be neutralized and removed from the system. This is currently carried out by the addition to the reaction mixture of a large amount of a base, sodium carbonate, to neutralize said by-product. While this means achieves the removal of the by-product hydrogen chloride, sodium carbonate is added in the solid state thereby requiring energy to thoroughly mix the solid carbonate in the liquid reaction product to achieve complete reaction. Furthermore, the neutralization reaction forms carbon dioxide gas and water that tends to provide foaming and caking problems and greatly slows the neutralization reaction. Consequently, it is likely that some of the hydrogen chloride is scavenged by methamphetamine forming methamphetamine hydrochloride. Higher reaction temperatures and longer reaction times are then needed to force the solid sodium carbonate to neutralize the solid methamphetamine hydrochloride and regenerate the reactive methamphetamine base. The tendency of solid sodium carbonate to form deposits on the walls and other internal surfaces of the reactor further reduces the effectiveness of such base added to the liquid reaction product.

In an attempt to improve the efficiency of the neutralization of by-product hydrogen chloride in the process for producing benzphetamine, other bases have been considered but all have demonstrated disadvantages that are prohibitive to their use. For example, triethylamine in the reaction mixture for the purpose of neutralizing by-product hydrogen chloride was determined to be unsatisfactory. Triethylamine has a boiling point of 85° C. that may suppress the 120° C. temperature range of the reaction mixture thereby causing significant refluxing. Also, such an amine may react with benzyl chloride forming benzyltriethylammonium salt. An amine that competes with the methamphetamine for the benzyl chloride is undesirable and the resulting quaternary ammonium salt may interfere with the isolation and purification of the product.

The literature contains reference only to sodium carbonate as a neutralizing agent for by-product hydrogen chloride in a reaction between methamphetamine and benzyl chloride to produce benzphetamine. Attempts to reduce the problems involved with acid by-product removal, has included reducing the addition of sodium carbonate and adding a diluent such as toluene to the reaction mixture. Also, slowing the rate of addition of benzyl chloride improved foaming condition but all such approaches were not considered sufficient improvements compared with the disadvantages involved with such modifications.

While the use of amines as described above have not shown sufficient advantage in the present reaction of interest, other reactions involving related compounds have employed amines to neutralize acid by-product. In U.S. Pat. No. 6,399,828, to Boswell et al. ammonium formate was employed in the catalytic hydrogenation reaction of O-acetylnorephedrine. In U.S. Pat. No. 5,536,877 there is disclosed a process for preparing aryl benzylamine by the reaction of aryl amines with a benzyl chloride in the presence of both a phase-transfer catalyst and an inorganic base. Excess base selected from inorganic bases and weak organic acids are employed. In U.S. Pat. No. 1,854,553 there is disclosed a process for preparing ethyl benzylaniline by the reaction of monethyl aniline and benzyl chloride in toluene. Soda ash is employed in the purification of the product.

To indicate the lack of predictability of attempts to neutralize acid by-product by means of amine-addition there is disclosed in U.S. Pat. No. 5,449,828 prior art problems with the preparation of propargyl ammonium chloride. It is disclosed therein that excess amine to bind excess hydrogen bromide in such process could not be employed because the problem of recovering the amine could not be solved. The neutralizing scheme disclosed in this patent employed an aqueous tartaric acid buffer system comprising ammonium hydroxide and basic alkali salts.

In U.S. Pat. No. 5,220,068, there are disclosed reactions to provide psycho stimulant agents by the reaction of various benzyl derivatives containing a halogen with alkyl amines or a halogenated amine with a benzyl amine. It is disclosed that various acid-binding agents may be employed including excess amine starting material, organic or inorganic bases or basic ion-exchange resins.

Other references disclosing the use of excess amine reactant include U.S. Pat. No. 5,198,587, a process for preparing phenethylamine and U.S. Pat. No. 2,987,548, a process for preparing benzylamine. In U.S. Pat. No. 2,490,813 there is disclosed a reaction of chlorobenzene with an organic amine in the presence of a copper chloride catalyst. An excess of amine was employed for the purpose of neutralizing the hydrogen chloride by-product. Also, a recycle scheme is disclosed wherein the excess amine was recovered and recycled to the reactor after basification to remove the hydrogen chloride from the amine. However, the process could not prepare a benzylamine because it employs a phenyl halide.

SUMMARY OF INVENTION

In accordance with this invention there is provided a novel process for the manufacture of a benzylamine by the reaction of the amine with a benzyl halide wherein the amine is in molar excess.

As employed herein the term "amine" refers to methamphetamine and propylhexedrine.

Although this invention is demonstrated with the use of benzyl chloride, it is clear that any benzyl halide may be employed. As employed in the specification and claims the "halide" means chlorine, bromine and iodine.

Preferably, the amount of excess amine is in molar excess in the range of about 2 to 1 with respect to benzyl halide. It has been discovered that the excess methamphetamine or propylhexedrine can be employed to selectively neutralize the by-product hydrogen halide. Excess amine reacts with the by-product hydrogen halide to produce the hydrohalide salt of methamphetamine or propylhexedrine. The hydrogen halide salt is typically crystalline and thus is easily removed from the reaction mixture by filtration as all other ingredients of the mixture are liquid. Further in accordance with this invention, the hydrogen halide salt of the amine recovered from the reaction medium is basified off line to recover the amine for recycle.

In another aspect of this invention, improved separation of the benzylated amine from the amine halide is achieved by the addition of an amount of water to the reaction mixture sufficient to dissolve the amine hydrogen halide thereby providing for a convenient liquid/liquid separation process whereby the benzphetamine/organic layer is isolated.

DETAILED DESCRIPTION

As noted above, while any suitable benzyl halide may be employed, the invention will be described with respect to the halide chlorine because it is most economically available for an industrial process.

The process of this invention is based upon the discovery that excess amine selectively neutralizes by-product hydrogen chloride in the reaction product containing the mixture of benzylated amine and starting amine. The improved selectivity for the HCl being scavenged by the excess amine instead of being scavenged by both the amine and the benzylated amine provides an extremely efficient and complete separation of the product from the by-products.

It is now believed that the selectivity referred to above as regarding the benzphetamine is based upon the difference in basicity as between methamphetamine and benzphetamine. It is observed that the pKa of benzphetamine is about 6.55 (Vree, T. B.; Muskens, A. Th. J. M.; Van Rossum, J. M., Journal of Pharmacy and Pharmacology (1969), 21(11), 774-5.) and the pKa of methamphetamine is about 10.11. (Id.) While it is not obvious that such difference in pKa of the materials would result is such a clear-cut difference in the neutralization of HCl in the reaction medium under reaction conditions, this discovery provides the basis for a very efficient system for the production of benzphetamine not heretofore available. Similar differences in pKa are expected with respect to propylhexedrine and benzylated propylhexedrine.

As noted above, the addition of an amount of water to the reaction mixture to dissolve the amine hydrochloride improves the separation of benzylated amine from amine hydrochloride. A small amount of the benzylated amine product also scavenges hydrogen chloride and may cause a yield loss. An effective and efficient method to achieve a nearly 100% separation of the benzphetamine base from the amine hydrochloride is to add water and then stir and heat the two liquid phases. This treatment causes the remaining unreacted amine base to basify the small amount of benzylated amine hydrochloride. The regenerated benzylated amine base is dissolved into the organic phase and the amine hydrochloride is dissolved in the water phase. Because the amine base is in the same phase as the benzyl chloride, it is more effective than sodium carbonate at scavenging the hydrogen chloride. As a result, the benzylation reaction of methamphetamine proceeds at temperatures as low as 85° C. whereas with sodium carbonate reaction temperatures of at least 100° C. were required for a complete reaction. Also, with methamphetamine as the HCl scavenger, the reaction is complete in half the time or less as compared with sodium carbonate.

As noted above, the facile removal of amine hydrochloride salt from the reaction mixture by any convenient solid/liquid separation method provides complete separation of the by-product acid more efficiently than heretofore realized. Another convenient alternative method to provide a complete separation of benzylated amine from amine hydrochloride is to add sufficient amounts of water to dissolve the amine hydrochloride thereby forming two phases, an aqueous phase and an organic phase. The two phases are then separated.

Further, there is no loss of starting material because the excess amine is easily recovered by reaction with any suitable base. Typically, any suitable base can be employed such as sodium hydroxide or potassium hydroxide or the like. It has been found most convenient to employ sodium hydroxide to basify the amine hydrochloride thereby rendering the recovered amine available for recycle to the reaction vessel. The process of this invention greatly increases efficiency due to significantly higher yields, increased reactor payload, shorter reaction times, recycle of the reactant and the elimination of large amounts of solid waste.

In the recovery process wherein the solid amine hydrochloride salt is separated from the liquid reaction product, it is usual to wash the solids to remove traces of product and to combine the wash liquor with the liquid reaction product. Typical agents employed to wash the separated amine hydrochloride salt include toluene, xylenes, benzene, and chlorobenzene. The preferred wash liquid is toluene. The separation and washing of a solid methamphetamine product is unnecessary when the solids are dissolved in water and the two liquid phases are separated. This method also provides for a higher product recovery and selectivity.

Typically a diluent is employed in the reaction mixture of the process of this invention to aid in mixing the reactants and thereby increasing the rate and completion of reaction. As the reaction proceeds in accordance with this invention an increase in solids occurs as the hydrochloride salt of the amine is produced. Such solids are crystalline in nature and are easily dispersed by mixing in a diluent. Any suitable diluent can be employed so long as it does not react with any of the contents of the reactor. Typical diluents include organic solvents such as toluene, xylenes and chlorobenzene. A preferred diluent is toluene.

Although there is some loss of efficiency in having to recycle the excess amine to the reaction vessel such minor loss is more than compensated by the advantages gained in the use of excess amine in the initial reaction mixture. For example, this invention eliminates one large volume raw material (sodium carbonate) from the process. Previously, sodium carbonate occupied up to about 29%, by weight, of the reactor charge. Because the process of this invention eliminates foaming in the reactor, greater initial charge to the reaction vessel is available thereby making up for the volume used for the amine requiring recycle. Since all the reactants are initially in liquid form, and amine is initially present at about 200% of the stoichiometrically required amount, it has been observed that the process of this invention provides a reduction of as much as 50% in reaction time cycle. Typically, there is a danger in recycling of product in that a build-up of impurities may occur. However, in the process of the present invention, it has been found that the impurities in the reaction mixture migrate to the benzylated amine/organic layer leaving the amine hydrochloride/aqueous layer. Thus, the amine hydrochloride is isolated in a highly pure state. The impurities are removed from the benzylated amine when it is purified by crystallization.

The process of this invention is illustrated below by the following examples that illustrate the practice of this invention but are not to be construed in a limiting sense.

EXAMPLE 1

To a 150 ml 3-neck flask fitted with a mechanical stirrer, a condenser and an addition funnel was added 23.12 g (0.1549 mole) of methamphetamine base. A nitrogen purge was started and maintained throughout the reaction to prevent the formation of colored by-products. The methamphetamine was stirred and heated to 100° C. Then 9.79 g (0.0773 mole) of benzyl chloride was added drop wise over a period of 23 minutes. Heat of reaction raised the temperature of the reaction mixture to 145° C. The reaction appeared to be instantaneous as the benzyl chloride was introduced. After the addition of the benzyl chloride was completed the reaction mass temperature dropped and heat was supplied to maintain a temperature of the reaction mass at 120° C. for a total of three hours. No foaming was observed. During the reaction methamphetamine hydrochloride precipitated out of the solution. As the mixture thickened a 15.74 g portion of toluene was added to aid mixing. After three hours the mixture was cooled to ambient temperature and vacuum filtered providing 13.48 g (98.8% yield after adjusting for samples taken during the reaction) on a dry basis of white methamphetamine hydrochloride crystals having a melting point of 172.4-178.4° C. (lit. 170-175° C.). An HPLC analysis found 92.5 area % methamphetamine and 3.8 area % benzphetamine. The product, benzphetamine base was in the filtrate and completely separated from the methamphetamine hydrochloride.

The separated benzphetamine base (68.70 g) in a toluene solution was converted to the hydrochloride salt by addition of 7.80 g of concentrated hydrochloric acid (37.5%). The salt was transferred to a separatory funnel and the 3-neck flask was rinsed with 16.60 g of water. The layers were separated into a 41.55 g water layer containing the benzphetamine hydrochloride and a 49.23 g toluene layer, which would contain any unreacted benzyl chloride.

The water layer containing the benzphetamine hydrochloride was transferred to a 300 ml 3-neck flask fitted with a mechanical stirrer and a Dean-Stark trap and condenser. The separatory funnel was then rinsed with 6.54 g of water. Then 190.1 g of toluene was added and the water was removed by azeotropic distillation. After water removal, the toluene was distilled forward until there was a total of 196.98 g of water/toluene distillate collected. Fresh toluene, 59 g, was then added to the 300 ml flask. The mixture was stirred and 46.49 g of toluene was distilled from the flask. The remaining mixture in the flask was cooled to ambient temperature, then slowly heated, whereupon rapid crystallization occurred. The mixture was then cooled to less than 10° C. to maximize product recovery. Vacuum filtration provided 20.77 g of benzphetamine hydrochloride wet cake and 42.41 g of filtrate. The wet cake was dried in a vacuum oven at 60° C. for 1.5 hours providing 18.59 g (89.4% yield after adjusting for samples taken) of white benzphetamine hydrochloride crystals having a melting point of 147.0-152.1° C. HPLC analysis found 94.9 area % benzphetamine and 4.3 area % methamphetamine. Such yield represents an improvement over the prior art procedure employing sodium carbonate to neutralize the HCl in the reaction mixture, which typically provided a yield of about 70%.

EXAMPLE 2

To a 100 ml 3-neck flask fitted with a mechanical stirrer, a condenser and an addition funnel was added 24.11 g (0.1615 mole) of methamphetamine base and 9.64 g of toluene. A nitrogen purge was started and maintained throughout the reaction to prevent the formation of colored by-products. The methamphetamine solution was stirred and heated to 120° C. Then 10.74 g (0.0848 mole) of benzyl chloride was added drop wise over a period of 40 minutes. After the addition of the benzyl chloride was completed the reaction mass temperature was maintained at 120° C. for a total of seven hours. No foaming was observed. During the reaction methamphetamine hydrochloride precipitated out of the solution. After seven hours the reaction mixture was cooled to about 70° C. and then 27.65 g of additional toluene and 50.84 g of water was added. The mixture was stirred and heated to 70° C. for 30 minutes. Then the mixture was cooled to ambient temperature and the two liquid layers were separated into a 65.28 g lower water layer containing the methamphetamine hydrochloride and a 51.47 g upper organic layer containing the benzphetamine base. An HPLC analysis found 99.8% of the methamphetamine partitioned to the water layer and 100% of the benzphetamine partitioned to the organic layer. The product, benzphetamine base was nearly completely separated from the methamphetamine hydrochloride. The yield of benzphetamine hydrochloride was 95% of the theoretical amount.

Similar results were obtained for the benzylation of propylhexedrine by the reaction of a benzylhalide with propylhexedrine wherein a molar excess of propylhexedrine, in the range of about 2 to 1 with respect to the benzylhalide, is employed.

EXAMPLE 3

To a 100 ml 3-neck flask fitted with a mechanical stirrer, a condenser, a thermocouple, and a nitrogen purge stream was added 1.9468 g (0.01254 mole) of propylhexedrine, 2.65 g toluene, and 0.79 g (0.00624 mole) of benzyl chloride. The reactor was continuously purged with nitrogen. The reaction mass was heated to 121° C. for 4.75 hr. A slurry of a crystalline solid in an oil formed. To this was added 4.60 g of toluene and 7.32 g of water. The mixture was vigorously stirred and heated to 50° C. for 10 minutes. The solids completely dissolved. After cooling, the two liquid phases were transferred to a separatory funnel. Water, (0.85 g) and a 1.62 g amount of toluene were used to rinse the residues in the flask into the separatory funnel. The layers were separated into a 9.10 g lower water layer containing the propylhexedrine hydrochloride and an 8.19 g upper organic layer containing the N-benzylpropylhexedrine. HPLC analysis of the organic layer found 20.76%, by weight, of benzylpropylhexedrine base which is 1.70 g (0.00692 mole) which is a 110% yield. The propylhexedrine hydrochloride in the water layer was converted to the base by adding 5.68 g of toluene and 1.18 g of 25% sodium hydroxide. The mixture was aggressively shaken. The layers were separated into a 9.05 g water layer having a pH of 13 and a 6.79 g toluene layer. The toluene layer was analyzed by gas chromatography and found to contain 13.10%, by weight, propylhexedrine base which is equivalent to 0.8895 g (0.00572 mole) or a 91.3% yield.

While this invention has been described with respect to various specific examples and embodiments, it is to be understood that the invention is not limited thereto.

The invention claimed is:

1. A process for the preparation of a benzylated amine with the co-production of by-product hydrogen halide, by the reaction of an amine selected from the group consisting of methamphetamine and propylhexedrine with a benzyl halide in a reaction vessel wherein said amine is in molar excess with respect to the benzyl halide and such excess reacts with by-product hydrogen halide to produce an amine halide.

2. The process of claim 1 wherein the molar ratio of amine to benzyl halide is about 2 to 1.

3. The process of claim 1 wherein the amine hydrogen halide is separated from the reaction mixture by solid/liquid separation means.

4. The process of claim 3 wherein the separation is performed by filtration means.

5. The process of claim 3 further including the step of basifying the amine hydrogen halide and recovering amine.

6. The process of claim 5 further including the step of recycling the amine to the reaction vessel.

7. The process of claim 1 further including the step of adding a diluent to the reaction mixture.

8. The process of claim 7 wherein the diluent is selected from the group consisting of toluene, xylenes, and chlorobenzene.

9. The process of claim 8 wherein the diluent is toluene.

10. The process of claim 1 wherein the amine hydrogen halide is dissolved in water and separated from the reaction mixture by liquid/liquid separation means.

11. The process of claim 1 further including the step of initially purging the reaction vessel with nitrogen.

12. The process of claim 1 wherein the halide is chlorine.

13. A process for preparing benzphetamine with the co-production of by-product hydrogen chloride by the reaction of methamphetamine with benzyl chloride comprising the steps of:
   A) combining the methamphetamine with benzyl chloride in a molar ratio of about 2 to 1, respectively, in a reaction vessel to produce benzphetamine and by-product hydrogen chloride;
   B) allowing the excess methamphetamine to react with by-product hydrogen chloride to produce a reaction mixture containing benzphetamine and methamphetamine hydrochloride salt;
   C) separating said methamphetamine hydrochloride salt from the reaction mixture;
   D) basifying methamphetamine hydrochloride to provide methamphetamine and isolating said methamphetamine, then;
   E) recycling the methamphetamine of step D to step A.

14. The process of claim 13 further including the step of providing an organic solvent diluent in steps A or B and in step C.

15. The process of claim 14 further including the steps, after separating said methamphetamine hydrochloride salt, of acidifying the remainder of the reaction mixture whereby said benzphetamine is converted to an acid salt, adding water to said reaction mixture to dissolve said acid salt and then separating the newly formed salt in water solution by liquid/liquid separation.

16. The process of claim 14 wherein the diluent is selected from the group consisting of toluene, xylenes, and chlorobenzene.

17. The process of claim 16 wherein the diluent is toluene.

18. The process of claim 14 further including in step C washing the separated methamphetamine hydrochloride to recover benzphetamine.

19. The process of claim 18 wherein the separated methamphetamine hydrochloride is washed with a washing agent selected from the group consisting of toluene, xylenes, benzene, and chlorobenzene.

20. The process of claim 19 wherein the washing agent is toluene.

21. The process of claim 13 wherein the methamphetamine hydrochloride is separated in step C by liquid/liquid separation by adding a sufficient amount of water so as to dissolve the methamphetamine hydrochloride and then separating the methamphetamine hydrochloride from the reaction mixture by liquid/liquid separation means.

22. The process of claims 13 further including the step of initialing purging the reaction vessel with nitrogen.

23. A process for preparing N-benzylpropylhexedrine with the co-production of by-product hydrogen chloride by the reaction of propylhexedrine with benzyl chloride comprising the steps of:
   A) combining the propylhexedrine with a benzyl chloride in a reaction vessel in a molar ratio of about 2 to 1, respectively to produce N-benzylpropylhexedrine and by-product hydrogen chloride;
   B) allowing the excess propylhexedrine to react with by-product hydrogen chloride to produce propylhexedrine hydrochloride to produce a reaction mixture containing N-benzylpropylhexedrine and propylhexedrine hydrochloride salt;
   C) separating said propylhexedrine hydrochloride from the reaction mixture;
   D) basifying propylhexedrine hydrochloride to provide propylhexedrine and isolating said propylhexedrine, then;
   E) recycling the propylhexedrine of step D to step A.

24. The process of claim 22 further including the step of providing a diluent in steps A or B and in step C.

25. The process of claims 24 further including the steps, after separating said propyhexedrine hydrochloride, of acidifying the remainder of the reaction mixture whereby said N-benzylpropylhexedrine is converted to an acid salt, adding water to said reaction mixture to dissolve said acid salt and then separating the newly formed salt in water solution by liquid/liquid separation.

26. The process of claim 24 wherein the diluent is selected from the group consisting of toluene, xylenes, and chlorobenzene.

27. The process of claims 26 wherein the diluent is toluene.

28. The process of claim 23 further including in step C washing the separated propylhexedrine hydrochloride to recover N-benzylpropylhexedrine.

29. The process of claim 28 wherein the separated propylhexedrine hydrochloride is washed with a washing agent selected from the group consisting of toluene, xylenes, benzene, and chlorobenzene.

30. The process of claim 29 wherein the washing agent is toluene.

31. The process of claim 23 wherein step C includes the step of adding a sufficient amount of water so as to dissolve the propylhexedrine hydrochloride and then separating the propylhexedrine hydrochloride from the reaction mixture by liquid/liquid separation means.

32. The process of claims 23 further including the step of initialing purging the reaction vessel with nitrogen.

* * * * *